United States Patent [19]

Pineda et al.

[11] Patent Number: 5,272,086
[45] Date of Patent: Dec. 21, 1993

[54] ARTIFICIAL ZONA PELLUCIDA FOR IN VIVO CULTURE OF NUDE BLASTOMERES

[75] Inventors: Mauricio H. Pineda, Ames, Iowa; John W. Pollard, Gainesville, Fla.

[73] Assignee: Iowa State University Research Foundation, Inc., Ames, Iowa

[21] Appl. No.: 125,257

[22] Filed: Nov. 25, 1987

[51] Int. Cl.$^5$ ............................................. C12M 3/00
[52] U.S. Cl. ....................................... 435/284; 600/33; 600/34; 604/29
[58] Field of Search .................... 435/284; 600/33, 34; 604/29

[56] References Cited

PUBLICATIONS

Wisniewski et al., In "Hydrogels for Medical & Related Applications", ed. Andrade, Amer. Chem. Soc. Symp. Series 31: 80-87 (1976).
Lee et al., J. Bioengineering 2: 269-278 (1978).
Ronel et al., J. Biomed. Materials Res. 17: 855-864 (1983).
Klomp et al., J. Biomed. Mat. Res. 17: 865-871 (1983).
Walladsen, Nature 277: 298-300 (1979).
Pinchuk et al., J. Biomed. Mat. Res. 15: 183-189 (1981).

*Primary Examiner*—Jasemine C. Chambers
*Attorney, Agent, or Firm*—Tilton, Fallon, Lungmus & Chestnut

[57] ABSTRACT

An artificial zona pellucida is provided for implantation in the peritoneal cavities of small laboratory animals. The assembly includes a hydrogel cartridge for containing one or more nude isolated blastomeres which can be cultured therein to an implant stage in the peritoneal cavity of a small animal such as a mouse. The combination is particularly advantageous for culturing of nude isolated blastomeres of a species different from the host small laboratory animal, such as blastomeres of domestic animals.

12 Claims, 2 Drawing Sheets

ARTIFICIAL ZONA PELLUCIDA FOR IN VIVO CULTURE OF NUDE BLASTOMERES

FIELD OF INVENTION

The field of this invention is mammalian embryo culture, and, in particular, the culturing of separated embryo cells to a stage at which they can be implanted.

BACKGROUND OF INVENTION

Although it is known that individual cells (blastomeres) of a developing mammalian embryo prior to the blastocyst implant stage are capable of developing into totipotent embryos, manipulation of embryos in the 2-, 4-, or 8-cell morulae stage has met with limited experimental success and has not developed into a commercial practice. Moore, et al. (1968) reported on a series of experiments with rabbit ova in which individual blastomeres were cultured in their own ova membrane (the zona pellucida). The culturing was compared with that of nude blastomeres without zona, and separated blastomeres inserted in the host zona. The culturing of the blastomeres was carried out in the fallopian tubes of the recipient does. No single blastomere devoid of zona survived, but survival was obtained with some of the blastomeres separated from the 2-, 4-, and 8-cell ova enclosed in their own zona, and the surviving blastomeres developed into normal rabbits. Separation of the blastomeres at the 2-cell stage gave a higher rate of survival (30%) than those separated at the 4- and 8-cell eggs (19% and 11%). Single blastomeres of 4-cell ova inserted in host zona showed limited development, undergoing one or more cleavages.

Isolated blastomeres and blastomere clusters prepared by microsurgery from pre-implantation embryos require some form of protection when the zona pellucida is removed or its integrity compromised (Moore, et al., 1968; Willadsen, 1979). Agar has been used to seal or encapsulate ruptured zona pellucida containing blastomeres (Willadsen, 1979). In the experiments reported by Willadsen, 2-celled sheep embryo were manipulated by severing the zona pellucida, removing and separating the blastomeres, and re-inserting a single blastomere into an evacuated zona. The zona-containing blastomeres were transferred to an agar solution held in the tip of a pipette until the solution hardened. A tiny solid cylinder of the agar containing the zona-encased blastomere was ejected. The small cylinders were encapsulated in larger solid cylinders of agar. The cylinders were transferred to ewe oviducts for incubation. After reaching the late morulae or early blastocyst stage, the agar cylinders were recovered, the agar was removed, and the embryos were implanted. Some live offspring were produced. The reduced embryo survival rate compared to standard embryo transfer was attributed to the difficulty of manipulating the embryos in the agar, which required the use of hypodermic needles, and other procedures.

The embedding of embryos in agar is referred to in the literature as the agar "chip" technique. The micromanipulations involved in the agar chip technique were summarized by Willadsen in 1982 in a treatise on "Mammalian Egg Transfer". After referring to the disappointing results in experiments on the developmental potential of isolated blastmeres, Willadsen concluded "with near certainty that the central problem in all instances arose from the lack of adequate methods for culture of the micromanipulated embryos in vitro in line with the inability of the embryonic cells to survive in vivo after the zona pellucida had been ruptured or removed". He further concluded that "none of the methods currently used is entirely satisfactory for the culture of early embryos, i.e., cleavage stages which are most dependent on the zona pellucida for their survival in vivo."

With reference to agar embedding, Willadsen (1982) had reported that "single blastomeres may be embedded without a zona pellucida, but this is not advisable, because it makes it very difficult to release the embryos at a later stage". Willadsen recommended that isolated blastomeres be contained in their own zona or in host zona, and that agar chip embedding be used only for such zona-contained blastomeres.

Egestone et al. (1985) reported on experiments in which 1-cell bovine embryos were embedded in agar and successfully cultured to the blastocyst stage in ewe oviducts. A tendency of the chips to dissolve in the oviduct fluid was observed. Boland (1984) reported on experiments using the rabbit oviduct as a screening tool for the viability of mammalian eggs embedded in agar chips. He concluded that the rabbit oviducts were unsuitable for such screening "because of the high rate of degradation of agar chips". More recently, Adaniya, et al. (1987) reported on the coating of rabbit embryos ready for implantation with sodium alginate. Following implantation in the uterus, the rate of degradation of the sodium alginate was observed. It was found that after four hours only 38% of the capsules remained, and after six hours none of the capsules were recoverable.

SUMMARY OF INVENTION

The present invention provides an artificial zone pellucida which can be used for culturing of isolated mammalian blastomeres, or blastomere clusters, without the use of any natural zona pellucida. The nude blastomeres are inserted directly in the artificial zone pellucida, which comprises a hollow cartridge of a size suitable for implantation in the peritoneal cavity or fallopian tube of a host mammal. The cartridge provides an enclosed incubation chamber having a chamber-enclosing wall formed of a cross-linked microporous hydrogel which is essentially non-biodegradeable. At least one viable nude mammalian blastomere is removably contained in the incubation chamber, and an aqueous culture medium is contained in the chamber in contact with the blastomere and the inside of the hydrogel wall. After implantation, transfer of substances from the fallopian or peritoneal fluid can take place through the hydrogel wall, thereby promoting the development of the blastomere to the blastocyst stage, ready for recovery and implantation.

For convenient insertion and removal of the blastomeres, the artificial zona pellucida cartridges can be provided with removable end plugs. If it is desired to culture more than one blastomere in the same cartridge, dividers may be provided within the cartridge separating the interior of the cartridge into a series of separate compartments. The dividers may also be made removable for convenient insertion and recovery of the embryos.

A preferred hydrogel material is a cross-linked methacrylate polymer, such as the hydrogel known as HEMA. HEMA consists primarily of polymerized 2-hydroxyethyl methacrylate. HEMA polymers may be cross-linked with glycol dimethacrylates, such as ethylene glycol dimethacrylate or tetraethylene glycol dimethacrylate. For purpose of the present invention, the cross-linking should not be so extensive that it prevents the hydrogel from functioning as a microporous membrane. In general, the amount of cross-linker employed should not be over 2.5 mole percent of the hydrogel.

THE DRAWINGS

Artificial zona pellucida assemblies constructed in accordance with the present invention are illustrated by the accompanying drawings, in which FIG. 1 is an exploded perspective view of a hydrogel cartridge;

DETAILED DESCRIPTION

Figure 1:
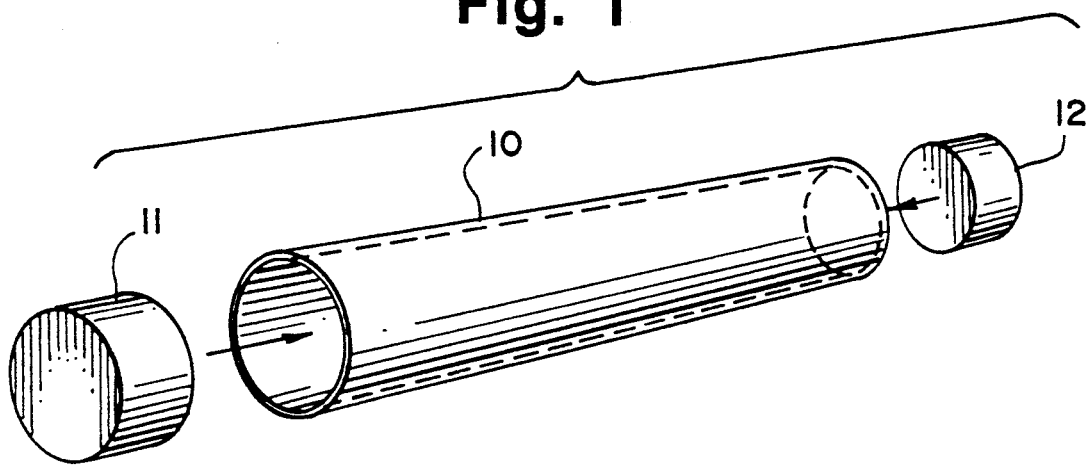

The artificial zona pellucida assembly of this invention can be employed for a number of different micromanipulations and culturings of mammalian embryos. In a preferred application, the assembly is employed for in vivo culturing of nude blastomeres, or clusters of nude blastomeres. For example, mammalian embryos in the morulae stage prior to blastulation can be separated by microsurgical techniques into individual blastomeres. Use of blastomeres derived from 2-, 4-, or 8-cell embryos can provide the means for the use of chimaeric production of multiple viable, totipotent embryos from a single fertilized ova. The techniques for separation and recovery of the blastomeres can be the same as previously employed. (See, for example, Willadsen, 1984.) Instead of individual nude blastomeres, clusters of two or four blastomeres can be used. For example, a 4-cell embryo can be separated into two-cell clusters.

For purpose of the present invention, the assembly comprising the artificial zona pellucida includes a hollow cartridge of a size suitable for implantation in a peritoneal cavity or fallopian tube of a host mammal. Where small mammals are to be employed, such as mice or rabbits, as may be preferred, the dimensions of the cartridge should be quite small, that is, the length may be from 1 to 3 cm and the exterior diameter from 3 to 5 mm. To achieve effective culture of the nude blastomere to the blastocyst stage, it is important that the body of the cartridge be formed from a microporous hydrogel.

Polymers of alkyl acrylates are known to form hydrogels which can be cross-linked to provide microporous structures. A preferred monomer for forming the hydrogel is 2-hydroxyethyl methacrylate (HEMA). HEMA can be polymerized in the presence of glycol dimethacrylate monomers which function as cross-linkers. Preferred cross-linkers are ethylene glycol dimethacrylate or tetraethylene glycol dimethacrylate. A limited degree of cross-linking is desirable. The swollen or hydrated membranes of cross-linked pHEMA should function essentially as pore-type membranes. They should also be essentially non-biodegradeable under the conditions of use. Solute transport should take place through water-filled regions of the hydrogel, which acts as the pores. At high cross-linking levels, the hydrogel membrane begins to function as a partition-type membrane. The solute interacts with the membrane matrix and diffusion is retarded. See Wisniewski, et al. (1976).

Data presented by Wisniewski indicated that cross-linked HEMA membranes up to about 2.5 mole % cross-linker can function essentially as microporous or pore-type membranes. For the purpose of this invention, it is therefore preferred that the hydrogel contain not over 2.5 mole percent of cross-linker, such as from 0.1 to 2.5 mole %. A preferred cross-linker range is from 0.2 to 1.0 mole percent in the hydrogel. Such exhibit high diffusivities as shown by Lee, et al., 1978). An optimum formulation is from 0.3 to 0.5 mole % of a glycol dimethacrylate cross-linker.

Procedures for preparing the cross-linked polymerized hydrogels are known. A mixture of the HEMA monomer and the cross-linker is prepared in the desired proportions using a suitable solvent such as ethylene glycol, or a mixture of ethylene glycol and water. Initiator solutions are also prepared, such as an aqueous solution of ammonium persulfate, and an aqueous solution of sodium metabisulfite. These reactants are combined under pressure to minimize the entrapment of bubbles in the hydrogel. A suitable pressure casting procedure using two hypodermic syringes is described in Pinchuk et al. (1981), and this procedure is also described in the following experimental examples.

It was found that the nude blastomeres could be loaded into the artificial zona pellucida tube using only sterile normal saline as the medium. This evidences that transfer of substances from the peritoneal or fallopian tube fluid, takes place and promotes blastomere development. It is preferred to use a starting medium which contains nutrients known to promote the growth of embryos or blastomeres. Whitten's medium (Whitten et al., 1968) supplemented with bovine serum albumin (BSA) can be used. Other suitable media for culturing embryos or blastomeres are described by Fisher (1987), Camous et al. (1984), and Brinster (1984). These include (suggest describing one or two suitable media.

The body cavity, referred to as the peritoneal cavity, is a suitable site for implantation of the artificial zona pellucida assembly in the host animal. For small laboratory animals, such as mice, hamsters, rabbits, etc., this is a more convenient site than the fallopian tubes. For implants in larger animals, such as sheep (ewes), the fallopian tubes can be used, and may be employed in ligated form. Means may be provided surgically for convenient insertion and removal in fallopian tubes. The fluid present in the peritoneal cavity of female mammals is similar to that found in its fallopian tubes (Bouckerchart, et al., 1986, and Bryans, et al., 1954). The peritoneal cavity of a female laboratory animal is preferred, such as a female mouse, it has been found that the peritoneal cavity of male laboratory animals can also be employed, although with somewhat less effective embryo development.

ILLUSTRATED EMBODIMENTS

Figure 2:
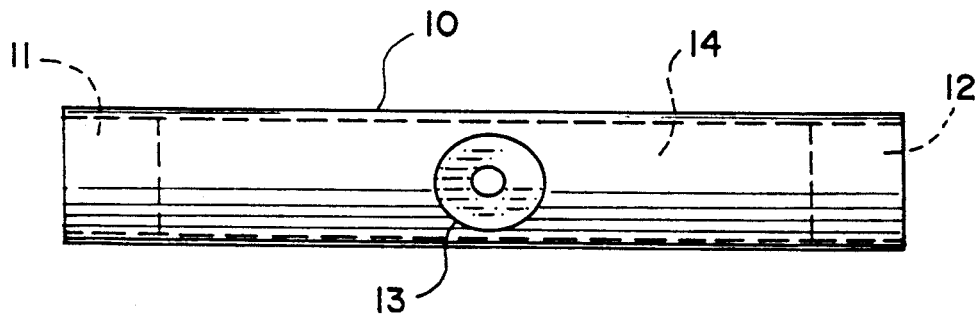
FIG. 2 is a side elevational view of the assembled cartridge of FIG. 1 containing a blastomere in an aqueous medium.

Several embodiment of the artificial zona pellucida assemblies of this invention are shown in the accompanying drawings. FIG. 1 represents a tubular hydrogel cartridge which is provided with end closures in the form of removable end plugs. The hydrogel cartridge is prepared from a cross-linked hydrogel as described above. Illustrative dimensions of the hydrogel cartridge shown in FIG. 1 include a chamber length of 1 cm, an outside diameter of 3.5 mm, an inside diameter of 1.7 mm, and a wall thickness of 0.9 mm. The wall thickness is given as 0.9 mm., but the wall thickness, as well as the other dimensions, may vary. Wall thicknesses within the range from 0.5 to 3 mm can be used. The end plugs 11 and 12 may be formed from a solid biocompatible polymer such as a silicone polymer. Alternatively, the end plugs may be formed of cross-linked HEMA, but transfer through the end plugs from the peritoneal or fallopian fluid is not required. In FIG. 2, the artificial zona pellucida of FIG. 1 is shown in assembled condition, containing a nude blastomere 13 immersed in a suitable aqueous medium 14.

Figure 3:
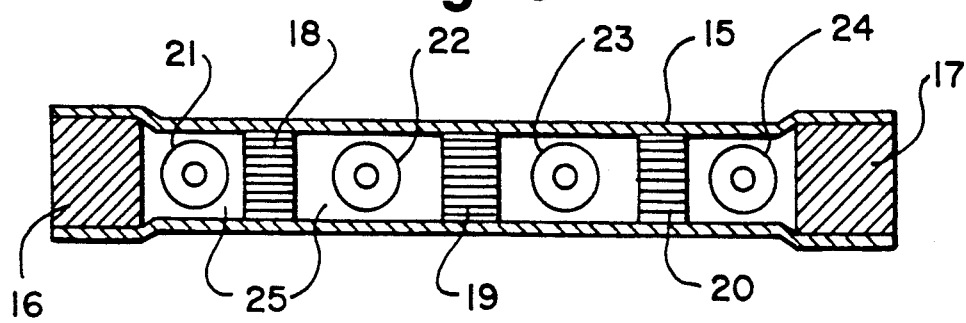
FIG. 3 is a sectional view of a modified hydrogel cartridge assembly including removable dividers which separate the cartridge chamber into a plurality of compartments receiving individual nude blastomeres.

In FIG. 3, there is shown, a multiple compartment artificial zona pellucida assembly 15. In this embodiment, the ends of the hydrogel cartridge are slightly enlarged to receive the removable end plugs 16 and 17. Within the cartridge there is provided three spaced removable dividers 18, 19 and 20. These dividers may be formed of cross-linked HEMA, or a non-permeable biocompatible plastic may be employed as a silicone polymer. The dividers separate the cartridge chamber into four compartments, and within each compartment there is provided a nude blastomere. This assembly permits the simultaneous culturing of four blastomers 21-24. Suitable aqueous media 25 will be employed within the compartments as previously described.

Figure 4:
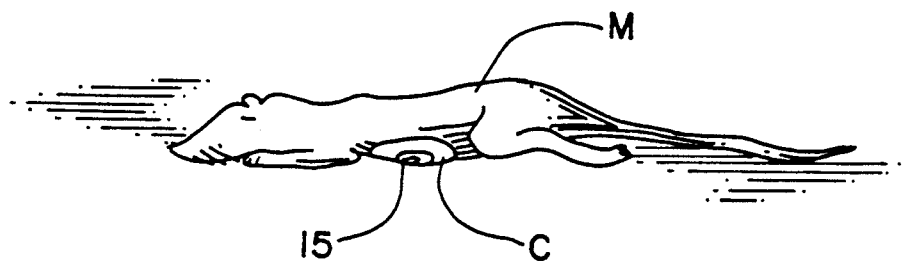
FIG. 4 is a diagrammatic view of a mouse with a portion of the mouse abdomen broken away to illustrate the insertion in the peritoneal cavity of the artificial zona pellucida assembly of this invention.

For culturing the artificial zona pellucida assemblies, such as the assembly of FIG. 2 or FIG. 3, the peritoneal cavity of a mouse may be used. A mid-line incision may be made in the abdomen of the mouse, the assembly inserted, and the incision sutured. The inserted artificial zona pellucida assembly 15 will normally rest in the lower portion of the peritoneal cavity C of the mouse M, as illustrated in FIG. 4. Instead of a host mouse, other laboratory animals may be employed, including rabbits, guinea pigs, hamsters, etc. While contained in the laboratory animal, such as the preferred mouse, the zona pellucida assembly may be shipped to a detination. Within shipping times of 2 to 4 days, such as by air transport, the nude blastomeres can continue to develop to the blastocyst stage, and will be ready for implantation when the host mouse or other laboratory animal reaches its destination.

Figure 5:
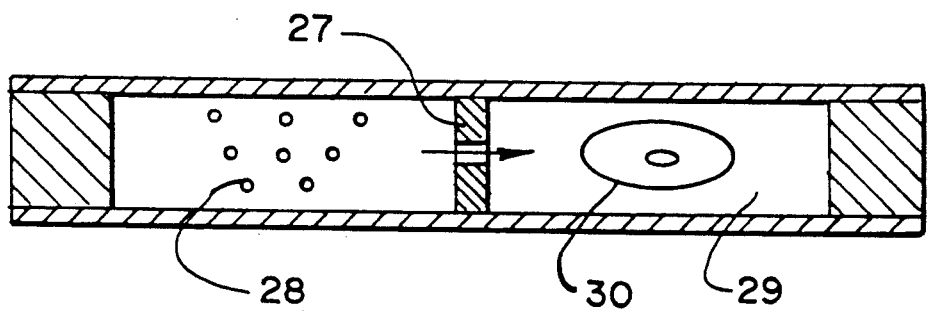
FIG. 5 is a sectional side elevational view of a modified hydrogel cartridge assembly which can be used for ova fertilization, including two chambers separated by a perforated divider, one for containing sperm and the other the ova to be fertilized.

The artificial zona pellucida of this invention may also be employed as an ova fertilization assembly 26, as illustrated in FIG. 5. The cConstruction of the hydrogel chamber and the end plugs is as previously described. A divider 27 is positioned centrally in the compartment. The divider may be formed from pHEMA or a silicone polymer, and is provided centrally with an opening of sufficient size to permit sperm to pass therethrough. Ova culture medium is provided in the compartments. In the left-hand compartment 28 viable sperm is placed and in the right-hand compartment 29 an unfertilized ova 30. To facilitate capacitance of the sperm and thereby obtain fertilization, the assembly may be placed in the vagina of a host animal. After fertilization occurs, the ova may be incubated in the cartridge until it is ready for implanting. Preferably on fertilization, the assembly is removed from the vagina and inserted in the peritoneal cavity or fallopian tube of the host animal. For embryo development, vaginal fluid is not as effective as peritoneal or fallopian fluid.

Figure 6:
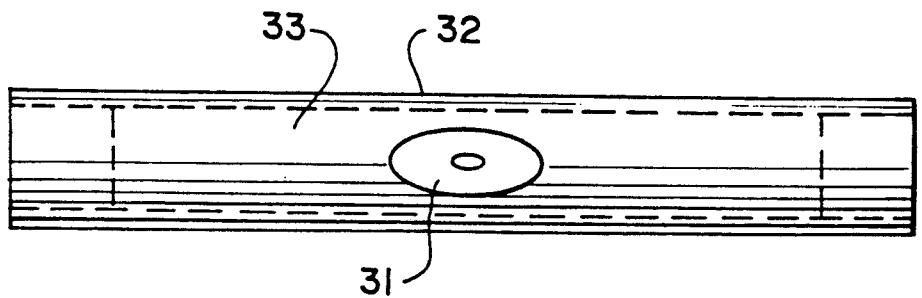
FIG. 6 is a view similar to FIG. 2, but illustrating use of the cartridge assembly as an incubator for a fertilized ova.

FIG. 6 illustrates a further use of the assembly. With the construction of FIG. 1, the fertilized ova 31 is placed within the hydrogel cartridge 32 and is surrounded with an aqueous ova culture medium 33. The assembly is then placed in the peritoneal cavity or fallopian tube of the host animal and retained therein until the ova develops to the implant stage.

The method of carrying out this invention and the results obtainable thereby are further illustrated by the following experimental examples.

EXPERIMENTAL EXAMPLES

Materials and Methods

Construction of Hydrogel Chambers

The hydrogel chambers were made from the mixture of HEMA monomer and tetraethylene glycol dimethacrylate (TGD) as the cross-linker. Ethylene glycol (DG) was used as a solvent. The formulation of reactants was that described by Lee et al. (1978, Table 1) for a ratio of 10 ml HEMA to 0.1 ml TGD. The mole % cross-linker in the hydrogel is approximately 0.4%.

Before casting the chambers, 3 stock solutions were prepared and placed in glass test tubes: Solution A—a mixture of 10 ml HEMA, 0.1 ml TGD, 3.0 ml EG, and 2.0 ml distilled water; solution B—initiator, 1.0 ml of ammonium persulfate, 40 g per 100 ml distilled water or 1.75 M; solution B—co-initiator, 1.0 ml of sodium metabisulfite, 15 g per 100 ml distilled water or 0.79 M. Each stock solution was purged with nitrogen and the reactants were mixed and polymerized under pressure, as described by Pinchuk et al. (1981) for the casting of ureteral anastomotic nipples.

The hydrogel chambers were case at room temperature within the barrel of 71 mm long, 3.5 mm ID, 0.5 ml insulin syringes (No. 8471 single use, plastipak LO-dose U-100; Becton Dickinson and Co., Rutherford, N.J.). The needle and its hub were removed to free the needed connector of the syringe. The plunger was withdrawn from the syringe and the rubber gasket at the tip of the plunger was removed and inverted so that the hollow cavity that previously attached the gasket to the plunger was directed toward the barrel of the syringe. The inverted gasket was then reinserted in the barrel and aligned with the 50-unit mark of the syringe. The syringe with the gasket in position was hand-held vertically with the needle connector directed upwardly. The reactants, 1.51 ml of Solution A, 0.1 ml o Solution B, and 0.1 ml of Solution C were then mixed within a 3 ml polyethylene syringe just before loading the casting insulin syringes. The syringe containing the polymerizing mixture was fitted with a 1½ inch (38.1 mm), 18-gauge needle, which was passed through the connector to fill the barrel of the insulin syringe with 0.5 ml of the polymerizing mixture. Immediately after filling the casting syringe, a 5.6 cm long, 0.9 mm OD stainless steel rod, inserted into a 5.6-cm long, 1.7 mm OD Teflon tubing (Cole-Parmer International, Chicago, Ill.) was passed through the needle connector and the mixture of reactants in the barrel of the insulin syringe to the rubber gasket in order to form a hollow chamber in the polymerizing gel. The Teflon tubing with the inserted steel rod was held in the center of the barrel by the needle connector and the hollow cavity of the inverted rubber gasket. A 6.0-cm long, 16 mm OD plexiglass rod, drilled through with a 7/32-inch bit (5.56 mm), was used to brace the barrel of the insulin syringe and prevent breakage during pressurized polymerization. A 4-cm long, 3.5 mm OD stainless steel rod was inserted into the flanged end of the barrel of the syringe and used to apply pressure to the gasket and polymerizing mixture. The braced syringe was then placed between size 9 neoprene stoppers attached to the jaws of a pipe claimp. Pressure was applied for 15 minutes by closing the jaws of the clamp until all visible air bubbles were displaced from the polymerizing gel. No attempt was made to measure the pressure applied with the clamp. After this 15-minute period of perssurized polymerization, the cast hydrogel was removed from the syringe and the centrally located Teflon tubing with the rod was withdrawn from the cast hydrogel which now was a hydrogel tube of approximately 5 cm long, with a 1.7 mm lumen and 0.9 mm thick wall. The pHEMA hydrogel tubes, in batches of 10 tubes, were then placed for 96 hours in a 100 ml glass beaker containing 95% ethanol which was changed every 12 hours to remove nonpolymerized HEMA. After ethanol washing, the pHEMA tubes were placed in a beaker containing 500 ml of distilled water, and heated at a slow boil for 4 hours. The distilled water was changed and the procedure repeated 12 times. After boiling, the pHEMA tubes were cut into 1 cm-long segments with a razor blade under observation with a stereoscopic microscope at 10X. Segments containing visible flaws were discarded. Solid plugs, 2 mm long were made from 0.085 inch (2.16 mm) OD Silastic tubing (Dow Corning Corp., Medical Products Midland, Me.) filled with Silastic adhesive and used to close the ends of the pHEMA tube to form a chamber, as illustrated in FIGS. 1 and 2. Each 1-cm segment of hydrogel tube and the 2 solid plugs to close the ends of the chamber were placed into a 2 ml glass ampulle (Wheaton Scientific, Millville, N.J.) containing distilled water. The ampulles were then autoclaved for 40 minutes at 120° C., fire-sealed, and stored at room temperature until used.

Animals

Twenty-three uniparous, crossbred rabbit does ranging from 1.0 to 1.5 years of age were used as embryo donors or recipients for Experiments 1 and 2. Does were individually caged for at least 21 days before assignment to the experiments, fed commercial rabbit food, and maintained during the experimental period in a room with controlled temperature (20° to 22° C.) and light (12 hours' light/12 hours' dark). Two crossbred, mature rabbit bucks of known fertility were individually caged, maintained in the same room, and fed, as described for the does.

Fifteen mature, cycling female and 10 mature male Balb/c mice were used as intermediate recipients for the 2 experiments of this study. Mice were caged by sex in groups of 4 to 5 females or 2 males per cage, fed commercial mouse food, and maintained in a room with controlled temperature (20° to 22° C.) and light (14 hours light/10 hours dark). For the female mice intermediate recipients, the stage of the estrous cycle was determined by vaginal smears and only females which were late in the afternoon of the day of estrus (D1) were used.

EXPERIMENT 1

Transfer of Rabbit Embryos Cultured in pHEMA Hydrogel Chambers in the Peritoneal Cavity of Intermediate Mouse Recipients.

Embryo Recovery and Culture

Ten does were randomly selected from the 23 does to serve as embryo donors and 10 does were selected to serve as recipients. To induce superovulation, each donor doe was given a subcutaenous injection of 0.5 mg of follicle-stimulating hormone (FSH-P, Burns Biotec, Omaha, Nebr.) every 12 hours for 72 hours. Donor does were mated twice to each of the 2 bucks, 24 hours after the last FHS injection. Each of the 10 mated donors was then randomly paired with a recipient. To synchronize donors and recipients, each unmated recipient was induced to ovulate by a single intramuscular injection of 50 IU of human chorionic gonadotropin (hCG, Fort Dodge Laboratories, Ft. Dodge, Iowa), given 14 hours after the fourth mating of the corresponding paired donor.

To recover 1-cell rabbit embryos, does were anesthetized with Halothane (Fort Dodge Laboratories, Ft. Dodge, Iowa) 18 hours after the 4th mating and each oviduct was flushed from the uterotubal junction with 3 ml of 0.9% (or 0.154 M sodium chloride) sterile saline solution. After flushing and recovery, embryos were examined with an inverted microscope at 100 × while still in the collecting dish and flushing fluid. Oocytes that had spermatozoa in the perivitelline space or embryos that had extruded the second polar body were considered to be 1-cell embryos. The 1-cell embryos from each doe were washed 3 times by trasnfer between 10×35 mm culture dishes (Lux, Miles Laboratories, Inc., Naperville, Ill.) containing sterile 0.9% saline solution before loading in the pHEMA hydrogel chambers.

Three pHEMA hydrogel chambers were prepared for each doe before embryo collection. The sealed tip of each glass ampulle was broken and the tube and plugs were withdrawn with sterile forceps and placed in 10×35 mm culture dishes containing sterile saline solution. With the aid of forceps, one of the solid plugs was inserted into one end of each of the 3 tubes and the tubes with the uninserted plugs were then incubated in a dish containing sterile saline solution for at least 110 minutes at 37° C., in an incubator with 5% $CO_2$ in humidified air, before loading the chamber with embryos.

The 1-cell embryos recovered from each donor doe were subdivided into 3 groups of equal numbers of embryos. The embryos from each group were transferred into the lumen of a saline solution-filled pHEMA tube, while the tube was immersed in sale. (The saline was used instead of an embryo media to confirm tranport from the peritoneal fluid through the hydrogel.) The open end of the tube was then sealed with the second Silastic plug and the sealed chambers were examined at 20× with a stereoscopic microscope to verify the number of embryos and the integrity of the chamber. The 3 chambers containing the embryos from each donor were then randomly assigned to one of the following treatment groups: Group 1: in vitro controls cultured for 72 hours in a 10×35 mm culture dish containing 3 ml of 0.9% sterile saline solution in an incubator at 37° C. with 5% $CO_2$ in humidified air; Group 2: cultured in vivo for 72 hours in the peritoneal cavity of an adult female Balb/c mouse on D1 of the cycle; Group 3: cultured in vivo for 72 hours in the peritoneal cavit of an adult male Balb/c mouse. The embryo-loaded chambers assigned to Groups 2 and 3 were surgically implanted in anesthetized (Metofane, Pitman-Moore, Washington Crossing, N.J.) female or male mice through a 1-cm long incision in the ventral abdominal wall. After 72 hours of either in vitro or in vivo culture, the chambers were recovered and examined at 25 to 100×with an inverted microscope to determine the stage of embryonic development. Embryos were classified as follows: Embryos that did not cleave or had fragmented blastomeres were considered degenerated; embryos that cleaved beyond the 1-cell stage, had recognizable, intact blastomeres, but did not reach the morula stage, were considered retarded; morulae were embryos that cleaved beyond the 16 cell stage but had not yet developed a blastocoele, while blastocysts were embryos with a clear, defined blastocoele. The number of degenerated or retarded embryos and the number of morulae and glastocysts obtained from each donor were recorded.

Embryo Transfer. The morulae and blastocysts obtained after in vivo culture in the pHEMA chambers were transferred to the paired recipient. Recipients were anesthetized with Halothane, as described for the donor does. The ventral area of the abdominal wall was clipped free of hair, disinfected, draped, and the uterine horns were exposed through a 6-cm long midventral incision. For each paired recipient, the left or right uterine horn was alternated as to receive embryos cultured in vivo in either male or female mouse. Each horn was punctured with the eye of a No. 22 suture needle and the embryos from treatment groups 2 or 3 were transferred to the lumen of the assigned horn using a 5 μl Wiretrol pipet (Fisher Scientific, Springfield, N.J.). The abdominal incision was sutured and each doe was fitted with an Elizabethan plastic collar until recovery from surgery.

Twenty-one days after transfer, recipient does were laparotomized. Before laparotomy, each doe was sedated by an intramuscular injection of 1 mg per kg of body weight of Acepromazine (Ceva Laboratories, Inc., Overland Park, Kans.). The midventral abdominal area was disinfected and then infiltrated with 10 mg/kg body weight of a 2% solution of Lidocaine (Astra Pharmaceutical Products, Inc., Worcester, Mass.). The uterine horns were exposed and the number of fetuses within each horn was recorded. Fetuses from embryos cultured in male mice were marked in utero by an injection of 1 μ of India ink deposited, as a subcutaneous drop, in the rump area of each fetus. At parturition, which occurred 6 to 8 days after laparotomy, the number of offspring derived from each of the 2 treatment groups was recorded. Bunnies were observed daily for general health until weaning.

Experiment 2

Blastomere Isolation and Culture in Compartmentalized pHEMA Hydrogel Chambers in the Peritoneal Cavity of Female Mouse Recipients.

Four-cell rabbit embryos were recovered from the 3 remaining does. Superovulation was induced and the embryos recovered, as described for Experiment 1, except that the oviducts were flushed 32 hours after the 4th mating with Whitten s medium (WM, Whitten and Biggers, 1968) supplemented with 1 mg bovine serum albumin (BSA, Fraction V, Sigma Chemical Co., St. Louis, Mo.) per ml of medium. The flushing medium was filtered through a 0.2 μm filter.

To isolate blastomeres, the 4-cell embryos recovered from each doe were placed in 10×35 mm culture dishes pretreated with Prosil 28 (PRC Inc., Gainesville, Fla.) to decrease adhesion of the blastomeres to the culture dish. The embryos were washed as a group 3 times at room temperature in filtered WV-BSA medium and then incubated for 15 minutes at 27° C. with 5% $CO_2$ in humidified air in $Ca^+$ and $MG^{++}$-free, modified Dulbecco's phosphate buffered saline solution (DPBS, Dulbecco and Bogt, 1954), supplemented with 0.02% (or 0.68 mM) EDTA and 0.25 M glycerol. Next the embryos were incubated for 15 minutes in modified DPBS, supplemented with 0.50 M glycerol and then transferred to Prosil 28 treated culture dishes containing modified DPBS supplemented with 1.0 M glycerol to remove the zona pellucida. The zona was removed under observation with inverted microscope at 100×with a hand-held microknife made from a piece of razor blade. The zona-free blastomere clusters were then transferred and incubated 2 times for 15-minute periods, first in a culture dish containing modified DPBS supplemented with 0.50 M glycerol and then in modified DPBS supplemented with 0.25 M glycerol. To separate the blastomeres, each blastomere cluster was transferred to a culture dish contianing modified DPBS only and then subjected, during observation with a stereoscopic microscope at 20×, to repeated aspiration into and expulsion from a 50 μm ID silicone coated capillary tube (Polymicro Technologies, Phoenix, Ariz.) attached to a 5 μl Wiretrol pipet. The isolated blastomeres were then washed 5 times by transfer between dishes containing WM-BSA medium. Only those embryos from each of the 3 donor does that yielded 4 intact blastomeres were used in this experiment. Th 4 blastomeres isolated from each embryo, hence a monozygotic group, were placed within individual compartments of a sterile pHEMA hydrogel chamber, under observation with a stereoscopic microscope at 20×. These chambers were made from HEMA, as described for Experiment 1, except that the length of each chamber was increased to 2 cm in length. One of the open ends was sealed with a plug and the lumen of the chamber was partitioned into 4 compartments, as illustrated in FIG. 3, by the insertion of 3, 1.7 mm OD×2 mm thick pHEMA discs, while in a 10×35 mm culture dish containing WM-BSA medium. The WM-BSA in the compartments served as the initial blastomere culture medium. These discs were made from HEMA hydrogel polymerized at room temperature within a 1.7 ID Teflon tubing without applying pressure. The first blastomere was placed in the chamber and one of the pHEMA discs was inserted in the lumen of the chamber and positioned at approximately 2.5 mm from the sealed end of the chamber. This procedure was repeated until each of the 4 blastomeres was loaded into the compartmentalized chamber, together with the WM-BSA medium. The chamber was then sealed with the remaining plub, as shown in FIG. 3. The chambers containing 4 isolated blastomeres were surgically implanted in the peritoneal cavity of a female Balb/c mouse on D1 and incubated in vivo for 72 hours as described for Experiment 1. Because of the number of monozygotic groups obtained, 4 chambers were implanted in the peritoneal cavity of each of 5 female mice. At the end of the 72-hour period of incubation, the compartmentalized chambers were recovered and the isolated blastomeres were examined for development with an inverted microscope at 25 to 100×.

Statistical Analysis

End points for stage of development of embryos cultured in vivo and for the results of transfer of morulae and blastocysts to recipient does between groups 2 and 3 of Experiment 1 were compared by Chi-square analysis, with 1 degree of freedom and Yates correction (Steel and Torrie, 1960). Significance was established at $P \leq 0.05$. Data for embryos cultured in vitro (control group 1 of Experiment 1) were not statistically compared with those of groups 2 and 3 due to the 0 values obtained.

RESULTS

Experiment 1

A total of 357, 1-cell embryos recovered from 10 donor does was used in this experiment (Table 1). all of the 238 embryos that were placed in the pHEMA chambers and cultured in vivo in the peritoneal cavity of male or female mice were recovered at the end of the 72 hours of in vivo culture, as reported in Table 1. All of the 119 embryos incubated in vitro in pHEMA chambers had degenerated during the 72 hours of culture. In comparison, only 10.1% cultured in male mice and 8.4% of the embryos cultured in female mice degenerated during the in vivo culture period. These differences were not significant ($P > 0.05$, Table 1). More ($P < 0.0005$ Table 1) of the embryos cultured in female mice developed to blastocysts (68/119) than those cultured in male mice (25/119). The transfer of 188 morulae and blastocysts (Table 1) recovered from pHEMA chambers implanted in the peritoneal cavities of male and female mice resulted in 23 (12.2%) live offspring, as shown in Table 2. Fewer ($P < 0.005$) offsprings were born from the transfer of embryos cultured in male mice (3/97, Table 2) than those cultured in female mice (20/81). Survival to term was not influenced ($P > 0.05$) by the horn to which embryos were transferred. The 23 bunnies developed in an apparently normal fashion and were released for adoption after weaning.

Experiment 2

A total of 43, 4-cell embryos was collected from 3 donor does and eighty intact blastomeres were isolated from 20 of these 4-cell embryos. All of the blastomeres that were cultured in vivo were recovered from the compartmentalized pHEMA chambers after the 72 hours of culture. Of these 80 isolated blastomeres, 16 (20%) were retarded or degenerated, 21 (26%) developed to the morula and 43 (54%) to the blastocyst stages, as shown in Table 3. Eleven (44 blastomeres) of the 20 originally cultured monozygotic groups developed, apparently in synchrony, to become either morulae or blastocysts. Including the 4 retarded blastomeres that cleaved but did not develop to the morula or blastocyst stages, 85% (68/80, Table 3) of the isolated blastomeres survived the isolation procedure and cleaved, while cultured in vivo in the compartmentalized pHEMA chambers. However, these de novo formed morulae and blastocysts were fragile and fragmented during withdrawal from the chamber.

DISCUSSION

In the present study, all of the embryos and blastomeres cultured within pHEMA chambers were recovered following the 72 hours period of culture. The development of 1-cell rabbit embryos to the morulae and blastocyst stages within saline-filled pHEMA chambers implanted in the peritoneal cavities of mice, as well as the birth of live offspring resulting from the transfer of these embryos, demonstrate that the pHEMA hydrogel chambers permit the passage of essential factors from the peritoneal cavity into the lumen of the chamber, such that embryonic development could occur. These results also confirm that the peritoneal cavity of mice can support the development of 1-cell rabbit embryos to the blastocyst stage (see Briones, et al., 1954.)

The percentage of 1-cell rabbit embryos that developed to the morula and blastocyst stages during culture for 72 hours in the peritoneal cavity of female mice is comparable to that reported for 2- and 4-cell embryos cultured within the ligated oviducts of estrous does (Adams, 1973). The development of embryos cultured in male mice was retarded when compared to the development of embryos cultured in female mice in our study or when compared to the rate of development in ligated oviducts (Adams, 1973). This suggests that the peritoneal cavity of the male mouse is a less favorable environment for embryonic development than that of the female mouse.

The percentage of offspring born from the transfer of morulae or blastocysts cultured from the 1-cell stage in the peritoneal cavity of female mice (20/91, 22%) appears to be greater than that resulting from embryos cultured in vitro for 72 hours (7.0%, Adams, 1970, 14%, Maurer, 1978) and compares with the percentages resulting from the transfer of 2 to 4-cell embryos cultured in the ligated oviduct of estrous does (17%, Adams, 1973) or obtained after transfer of noncultured embryos to asynchronous recipients (27%, Yang, et al., 1986).

The fewer offspring born from the transfer of 1-cell rabbit embryos cultured in the peritoneal cavity of male mice (3/97, 3%) could be the result of the transfer of more morulae than blastocysts (72 morulae and 25 blastocysts, Table 2) than for the female mice (23 morulae and 68 blastocysts).

The number of isolated blastomeres that developed during in vivo culture to morulae and blastocysts, while contained in the compartmentalized pHEMA chambers, as well as the recovery at the end of the incubation period of all of the resulting product of each of the isolated blastomeres, attest to the protective nature of the pHEMA chamber. The development of apparently normal blastocysts and the lack of trophoblastic vesicles in the blastocysts derived from isolated blastomeres suggests complete development while in the pHEMA chamber.

In summary, the results of this study demonstrate that pHEMA hydrogel can be cast into sealable and easily retrievable chambers for the in vivo culture of embryos.

TABLE 1

| Treatment | Number of Embryos | | | | |
|---|---|---|---|---|---|
| | Cultured | Degenerated | Retarded[a] | Morula | Blastocyst |
| In Vitro Controls | 119 | 119 | 0 | 0 | 0 |
| Male Mouse | 119 | 12 | 10 | 72* | 25 |
| Female | 119 | 10 | 18 | 23 | 68* |

TABLE 1-continued

| Treatment | Number of Embryos | | | | |
|---|---|---|---|---|---|
| | Cultured | Degenerated | Retarded[a] | Morula | Blastocyst |
| Mouse | | | | | 5 |

[a]Embryos that cleaved beyond the 1-cell but did not advance to the morula stage.
*Significantly (P < 0.0005) different from the corresponding in vivo treatment group.

TABLE 2

| Recipient number | Sex of intermediate mouse recipient | Number (stage)* transferred | Uterine horn | Fetuses day 25** | Offspring born alive |
|---|---|---|---|---|---|
| 1 | male | 7 (M), 3 (B) | left | 0 | — |
| | female | 1 (M), 9 (B) | right | 0 | — |
| 2 | male | 8 (M), 4 (B) | right | 0 | — |
| | female | 11 (B) | left | 3 | 3 |
| 3 | male | 6 (M), 2 (B) | left | 0 | — |
| | female | 9 (B) | right | 3 | 3 |
| 4 | male | 10 (M), 1 (B) | right | 0 | — |
| | female | 13 (B) | left | 4 | 4 |
| 5 | male | 7 (M), 1 (B) | left | 0 | — |
| | female | 7 (M) | right | 0 | — |
| 6 | male | 7 (M), 2 (B) | right | 0 | — |
| | female | 1 (M), 7 (B) | left | 2 | 2 |
| 7 | male | 11 (M), 2 (B) | left | 1 | 1 |
| | female | 3 (M), 9 (B) | right | 4 | 4 |
| 8 | male | 5 (M), 5 (B) | right | 2 | 2 |
| | female | 9 (B) | left | 4 | 4 |
| 9 | male | 7 (M), 1 (B) | left | 0 | — |
| | female | 6 (M) | right | 0 | — |
| 10 | male | 4 (M), 4 (B) | right | 0 | — |
| | female | 5 (M), 1 (B) | left | 0 | — |
| Totals | male | 97 (72M), (25B) | — | 3 | 3 |
| | female | 91 (23M), (68B) | — | 20 | 20 |

*Stage:
(M), morula;
(B), blastocyst.
**Determined by laparotomy on day 25 of gestation.

TABLE 3

| Blastomeres isolated and cultured | 80 |
|---|---|
| Of these ... | |
| Degenerated | 12 |
| Retarded[a] | 4 |
| Morulae | 21 |
| Blastocysts | 43 |
| Total recovered after culture | 80 |
| Total developing to the morula or blastocysts stages | 64 [11] |

[a]Blastomeres that cleaved but did not advance to the morula or blastocyst stages.
[ ] Brackets indicate monozygotic groups.

REFERENCES

Adams, 1973. The development of rabbit eggs in the ligated oviduct and their viability after re-transfer to recipient rabbits. *J. Embryol. Exp. Morphol.* 29:133–144.

Adanyi, et al., 1987. Comparison of in vitro and in vivo degradation rates for encapsulated preimplantation embryos. Proc. 20th Anniversary Meeting Soc. Study Reporod., Urbana, Ill., Jul. 20–23, 8, Abstract 403.

Boland (1984). Use of the rabbit oviduct as a screening tool for the viability of mammalian eggs. *Theriogenology* 21:126–137.

Brinster, 1969. In vitro cultivation of mammalian ova. In: Raspe, G. (ed.), Advances in the Biosciences 4. New York: Pergamon Press, pp. 199–232.

Briones, et al., 1954. Interspecific transfers of rodent eggs. J. Exp. Zool. 125:99–118.

Bouckaert et al. (1986). Patterns of change in proteins in the peritoneal fluid of women during the periovulatory phase of the menstrual cycle. *J. Reprod. Fert.* 77:329–336.

Camous, et al., 1984. Cleavage beyond the block stage and survival after transfer of early bovine embryos cultured with trophoblastic vesicles. *J. Reprod. Fertil.* 72:479–485.

Eyestone, et al., 1985. Culture of 1-cell bovein embryos in the sheep oviduct. Proc. 18th Ann. Meeting Soc. Study Reprod., Montreal, Canada, Jul. 22–25, 1985, Abstract 125.

Fisher, 1987. Development retardation in cultured preimplantation rabbit embryos. *J. Reprod. Fertil.* 79:115–123.

Lee et al. 1978 Solute transport through crosslinked poly (2-hydroxyethyl methacrylate) membrane. J. Bioeng., 2:269–278.

Maurer (1978). Advances in rabbit embryo culture. In: Daniel, J. G., Jr. (ed.), Methods in MAmmalian Reproduction. New York: Academic Press, pp. 259–272.

Moore, et al. (1968). Developmental potential of single blastomeres of the rabbit egg. *J. Reprod. Fertil.* 17:527–531.

Pinchuk, et al., 1981. Pressurized polymerization for reaction casting of poly (2-hydroxyethyl methacrylate). *J. Biomed Mat Res.,* 15:183–189.

Whitten, et al., 1968. Complete development in vitro of the preimplantation stages of the mouse in a simple chemically defined medium. *J. Reprod. Fertil.,* 17:399–401.

Willadsen, 1979. A Method for culture of micromanipulated sheep embryos and its use to produce monozygotic twins. *Nature* 277:298–300.

Willadsen, 1982. Micromanipulation of embryos of the large domestic species. In: Adams (ed.), Mammalian Egg Transfer. Boca Raton: CRC Press, pp. 185–210.

Yang, et al., 1986. Asynchronous embryo transfer in rabbits. Proc. 12th Ann. Conf. Int. Embryo Transf. Soc., Colorado Springs, Jan. 12–14 1986, Abstract. Theriogenology, 25:219.

Wisniewski, et al., 1976. Diffusion through hydrogel membranes. In: "Hydrogels for Medical and Related Applications," ed. J. D. Andrade, Amer. Chem. Soc. Symp. Series, No. 31, pp. 80–87.

We claim:

1. An artifical zona pellucida assembly suitable for implantation in the peritoneal cavity of a small laboratory animal, said assembly comprising a hollow cartridge of a size suitable for implantation in said peritoneal cavity said cartridge providing an enclosed incubation chamber and having a chamber-enclosing wall formed of cross-linked microporous hydrogel, at least one nude isolated mammalian blastomere of a species different than the laboratory animal contained within said chamber, and an aqueous culture medium in said chamber in contact with said blastomere and the inside of said hydrogel wall.

2. The assembly of claim 1 in which said cartridge is tubular with open ends, and closure lugs are removably received in said ends.

3. The assembly of claim 1 or claim 2 in which said incubation chamber has at least one removable divider arranged to subdivide said chamber into a plurality of separate incubation compartments, and at least one of said blastomeres is contained within each of said compartments.

4. The assembly of claim 1 or claim 2 in which said hydrogel wall is formed from polymerized cross-linked 2-hydroxyethyl methacrylate (HEMA), which hydrogel contains not over 2.5 moles percent of cross-linker.

5. An artificial zona pellucida assembly suitable for implantation in the peritoneal cavity of a small laboratory animal said assembly comprising a tube of a size suitable for implantation in said peritoneal cavity, removable end plugs for said tube to provide an enclosed incubation chamber, said tube being formed of cross-linked microporous hydrogel which under the conditions of use is non-biodegradeable, at least one viable nude isolated mammalian blastomere of a species different than the laboratory animal contained within said chamber, and a culture medium in said chamber in contact with said blastomere and the inside of said hydrogel tube.

6. The assembly of claim 5 in which said tube has a wall thickness of from 0.5 to 3 millimeters (mm).

7. The assembly of claim 5 or claim 6 in which said hydrogen is formed from polymerized cross-linked 2-hydroxyethyl methacrylate (HEMA) and which hydrogel contains from 0.2 to 1.0 mole percent of cross-linker.

8. The combination of claim 5 or claim 6 in which said tube is formed from polymerized cross-linked 2-hydroxyethyl methacrylate (HEMA) which is cross-linked with a glycol dimethacrylate selected from the group consisting of ethylene glycol dimethacrylate and tetraethylene glycol dimethacrylate, said cross-linked hydrogel containing from 0.2 to 1.0 mole percent of said cross-linker.

9. An artificial zona pellucida assembly suitable for implantation in the peritoneal cavity of a small laboratory animal said assembly comprising a hollow cartridge of a size suitable for implementation in said peritoneal cavity, said cartridge providing an enclosed incubation chamber and having a chamber-enclosing wall formed of cross-linked microporous hydrogen, said hydrogel being composed of polymerized 2-hydroxyethyl methacrylate (HEMA) cross-linked with a gycol dimethacrylate selected from the group consisting of ethylene glycol dimethacrylate and tetraethylene glycol dimethacrylate, at least one viable nude isolated mammalian blastomers of a species different than the laboratory animal removably contained within said chamber, and an blastomers culture medium in said chamber in contact with said blastomers and the inside of said hydrogel wall.

10. The assembly of claim 9 in which said hydrogel wall has a thickness of from 0.5 to 3 millimeters (mm), and said cross-linker is present in said hydrogel in an amount of 0.1 to 2.5 mole percent.

11. The assembly of claim 9 or claim 10 in which said cross-linker is present in said hydrogen in an amount of from 0.2 to 1.0 mole percent.

12. The assembly of claims 1, 5, or 9 in which said small laboratory animal is a mouse.

* * * * *